United States Patent [19]

Filhol

[11] 4,371,342
[45] Feb. 1, 1983

[54] DENTAL ANCHORING MEANS

[76] Inventor: Stuart J. Filhol, Castlefrek, County Cork, Ireland

[21] Appl. No.: 258,651

[22] Filed: Apr. 29, 1981

[30] Foreign Application Priority Data

Apr. 29, 1980 [GB] United Kingdom ............... 8014134

[51] Int. Cl.³ ................................................ A61C 5/04
[52] U.S. Cl. ........................................ 433/225; 433/128
[58] Field of Search ................ 433/128, 215, 225, 165

[56] References Cited

U.S. PATENT DOCUMENTS 4,205,444 6/1980 Weissman ........................ 433/128

Primary Examiner—Robert Peshock
Attorney, Agent, or Firm—Gifford, VanOphem, Sheridan and Sprinkle

[57] ABSTRACT

Dental anchoring means includes a cylindrical shank having a turned over portion at one end and an integral threaded pin at the other end which is detachable from the shank.

The anchoring means locates in holding means in the form of a sleeve with a longitudinal opening. The shank extends through the opening and is held for rotation with the sleeve by a stop member at one end of the sleeve which engages the turned over portion.

The sleeve is located as a gear wheel in a dental handpiece which may be a self-contained unit.

7 Claims, 3 Drawing Figures

U.S. Patent     Feb. 1, 1983     4,371,342
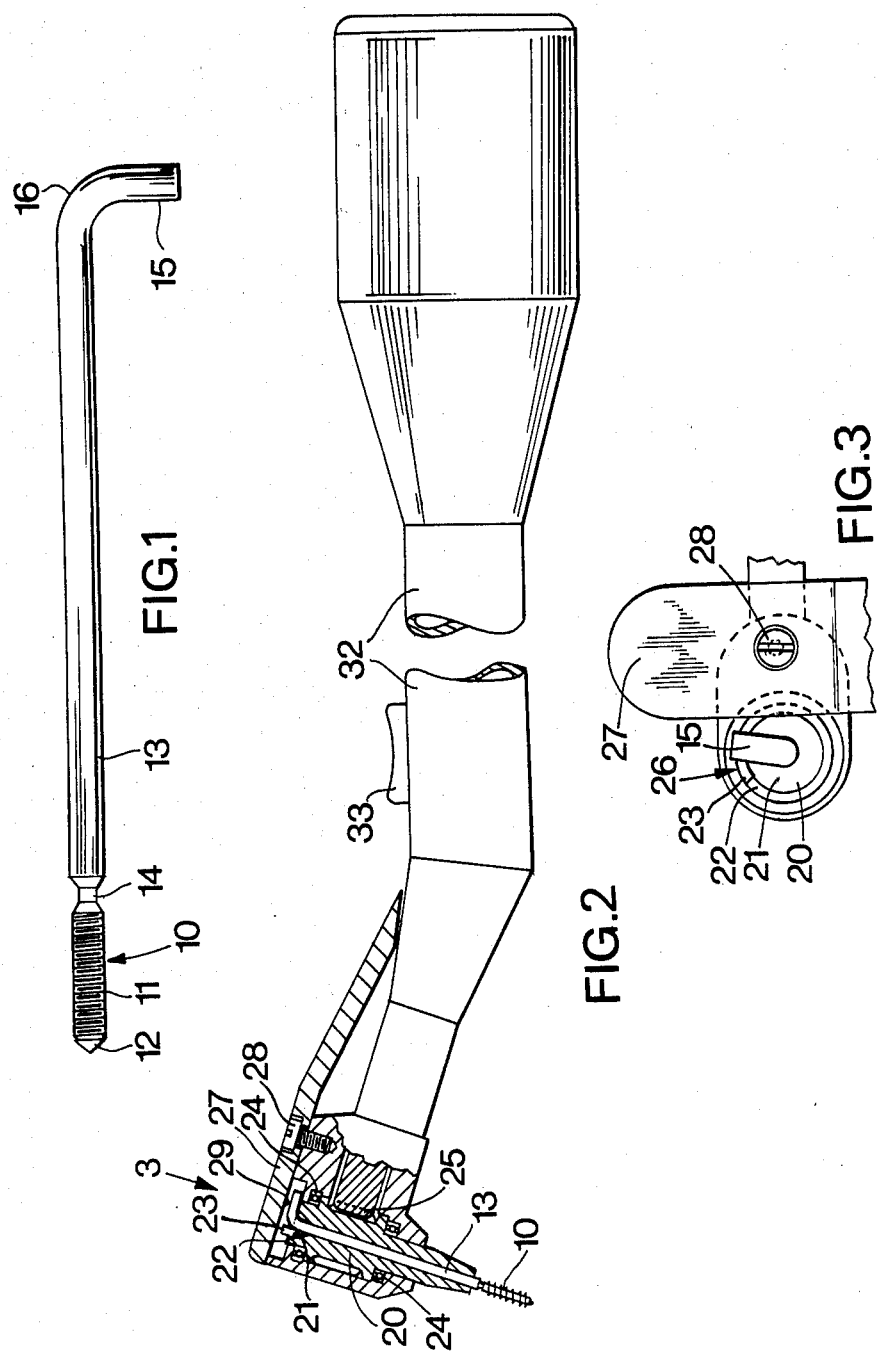

4,371,342

DENTAL ANCHORING MEANS

BACKGROUND OF THE INVENTION

1. Field of the Invention

This invention relates to dental anchoring means and in particular to dental pins and an arrangement for inserting dental pins into teeth.

2. Description of the Prior Art

Dental anchoring pins have been proposed for use in anchoring built up superstructures onto teeth. For example in British Pat. No. 1,347,227 there is proposed a threaded pin releasably attached to a shank, the shank being arranged for location in a handpiece for insertion of the pin. Operation of the handpiece rotates the pin to drive the pin into a preformed hole in the tooth. The shank includes location means for holding the shank on a rotatable portion of the handpiece but the manner of location causes a risk of the shank and pin becoming detached from the handpiece and falling into the mouth of the patient. In British Pat. No. 1,482,681 there is proposed a similar dental pin and shank combination but in this case the shank has a positive locking arrangement for preventing inadvertent release of the shank from the handpiece. However the arrangement of the shank makes it relatively costly to produce and this is especially disadvantageous in view of the need for the shank to be a throw-away item after release of the pin.

In British patent application No. 2016631 there is disclosed a dental pin having a plastics shank which holds a metal dental anchor, a threaded portion of which is detachable upon insertion into a tooth. The anchor includes wings and is a force fit in the shank. After use the shank, which is shaped to fit the standard dental handpiece, and the remaining metal anchor part are thrown away.

SUMMARY OF THE PRESENT INVENTION

Thus it can be seen that dental pins have either been of integral construction with a shank portion including a profile to fit standard dental hand piece locating mechanisms, or the pins have been fitted to an adaptor incorporating a profile to fit said latching mechanism. In each case the profiled shank or adaptor are usually discarded after use and the cost of these items should therefore be relatively little. It is advantageous in principle that the dental pin and its associates shank should be formed in one piece, i.e. of integral construction, to reduce the possibility of the shank and pin become separated and falling in the patient's mouth. It is also important that the shank should be securely latched on the handpiece, for the same reason. The present standard latching mechanism is generally satisfactory in retaining the shank in the handpiece but it imposes costly requirements on dental pin constructions, particularly in the case of dental pins with integral pin and shank constructions in which the profile to fit the latching mechanism has to be machined in metal.

It is an object of the present invention to provide a construction of dental anchoring means which is securely retained in a dental handpiece, which means may be of integral construction and inexpensive to produce.

According to one aspect of the invention dental anchoring means comprises a shank section and a threaded dental pin section detachably secured to one end of the shank section for detachment of the pin section from the shank section when the pin is screwed into a tooth, the shank section being securable in a handpiece for screwing the pin section to a tooth, wherein the end of the shank section remote from the pin section is turned over to define a substantially L-shaped securing portion.

The invention also provides in combination dental anchoring means and holding means for the anchoring means, the anchoring means comprising a shank section and a threaded dental pin section detachably secured to one end of the shank section for detachment of the pin section from the shank section when the pin is screwed into a tooth, the shank section being securable in a handpiece for screwing the pin section into a tooth; the holding means comprising a rotatable member having a longitudinal opening for receiving the shank section, the rotatable member being located in said handpiece; wherein said shank section at its end remote from the pin section is turned over to define a securing portion, and the longitudinal opening in the rotatable member extends from one end of the member to the other end so that the anchoring means can be inserted through the opening for the securing portion to engage with a stop member on the rotatable member for rotation of the anchoring means with the rotatable member.

Preferably the holding means includes a securing member attached to said handpiece and movable to be locatable over the end of the longitudinal opening at which said stop member is located to retain the anchoring means in said rotatable member.

Conveniently the securing portion of the shank section is substantially L-shaped and the shank section is of circular cross-section.

The rotatable member is conveniently located in bearings in the handpiece and located around, as a close fit, the length of the shank.

BRIEF DESCRIPTION OF THE DRAWING

Further features of the invention appear from the following description of an embodiment of the invention given by way of example only and with reference to the drawings, in which:

FIG. 1 is an elevation of an anchoring device;

FIG. 2 is an elevation partly in section of a handpiece for the anchoring device of FIG. 1, and FIG. 3 is a view in the direction of arrow 3 in FIG. 2 to a larger scale with a part of the handpiece moved.

DETAILED DESCRIPTION OF THE PREFERRED EMBODIMENT OF THE PRESENT INVENTION

Referring to the drawings and firstly to FIG. 1 an anchoring device includes a threaded self-tapping metal pin section 10 which may be of conventional form having a threaded profile over surface 11 with a tapered leading end 12. The pin section 10 may take the form disclosed in British Patent Specification No. 1,580,356 and may be made of any suitable material suitable for dental work, such as stainless steel or titanium.

The pin section 10 is integral with a circular section cylindrical shank section 13 to which it is joined through a reduced section portion 14 which serves as a break-off point after insertion of the pin 10 in a tooth, in known manner. The shank 13 is turned over at its end remote from the pin 10 to provide a turned-over portion 15. The portion 15 lies at a right angle to the shank 13 and is joined thereto over an arc 16 to define an L-shaped member.

The anchoring device of FIG. 1 is fitted in the handpiece of FIGS. 2 and 3 for screwing the pin 10 into a tooth. The handpiece includes a rotatable sleeve 20 which is formed with an axial cylindrical opening which is substantially the same diameter as the shank 13 and in which the device locates as shown. The opening is tapered outwardly at 21 at one end to receive the device and an annular portion 22 of the sleeve around the tapered portion 21 is formed with one or more integral pins or stop members 23. Thus when the device is located in the sleeve the turned-over portion 15 of the shank is drivingly engaged by the pin 23.

The sleeve 20 is located in bearings 24 carried in one end of the handpiece and the sleeve constitutes a gear wheel 25 by which the sleeve is drivingly connected to drive means in the handpiece. The handpiece has an opening at 26 through which the anchoring device is inserted into the sleeve and the opening 26 is closed in use by a plate 27 pivotable about a pin 28 from an open position, as shown in FIG. 3, to a closed position, as shown in FIG. 2. The lower surface 29 of the plate 27 is closely adjacent the pin 23 and the portion 15 of the shank so that in the closed position said surface 29 acts as a bearing surface and prevents disengagement of the device from the sleeve 20.

The handpiece incorporates a drive motor in a housing 31, which is conveniently a battery-operated electric motor or a constant torque spring motor, and drive is taken from the motor by drive shafts and bevel gearing (not shown) in the body 32 of the handpiece. A stop/start button 33 is provided on said body 32 to actuate the motor and rotate the sleeve.

It will be seen that the handpiece differs from the conventional high speed, air motor-powered handpiece hitherto used for drilling the holes and for inserting anchoring devices. The present handpiece is self-contained and has a high torque, slow speed motor.

This is advantageous since the insertion of the device involves relatively few rotations of the pin to achieve full insertion and the separate, self-contained handpiece is immediately available for use after a drilling operation using another handpiece.

The anchoring device of the invention is very simple to make in requiring only the pin to be formed and the end of the shank to be bent over to form the turned over portion. The throw-away shank portion is a low cost item giving overall cost savings.

The shank and pin are positively located in the handpiece so that they cannot inadvertently fall out and the device is easily inserted and removed from the handpiece. Since the cover plate cannot be correctly located unless the device is in position in the handpiece, the user is assured of correct location before use. The pin 10 and shank 13 are of integral construction but a shank and pin of non-integral construction could also be employed, if desired.

The provision of the turned-over portion of the shank enables the device to be more readily picked out of a pack in which the devices are stored.

It will be seen that the shank section 13 is supported over its length, the lower part of the shank being enclosed by a tapered extended portion of the sleeve 20 projecting from the handpiece, so that the device is adequately supported in use.

Instead of a threaded anchoring pin the shank may be formed on one end with a drill section for drilling the holes in the tooth which are to receive the anchoring pin and the handpiece may be used to perform both operations.

The anchoring means of the invention is simple to make and, therefore, inexpensive. The anchoring means is always securely located in the handpiece in use and, by the use of the special handpiece, the insertion of dental pins becomes a simpler and quicker operation.

What I claim as my invention and desire to secure by Letters Patent of the United States is:

1. In combination dental anchoring means and a dental handpiece for receiving the anchoring means; the anchoring means comprising a shank section and a threaded dental pin section detachably secured to one end of the shank section, said pin section adapted for detachment from the shank section when the pin section is screwed into a tooth, the shank section having at its end remote from the pin section a turned-over securing portion; the dental handpiece means for holding the anchoring means, said holding means comprising a rotatable member having a longitudinal axial bore for receiving the shank section, said dental pin section projecting through an end of said bore, said dental handpiece comprising powered means for rotatably driving the rotatable member, wherein the improvement comprises defining the rotatable member as a sleeve in which the bore is open-ended, the pin section projecting through one, lower end of the bore and at the other, upper end of the bore the rotatable member having a stop member, the dental anchoring means being locatable through the bore with said turned-over portion engaging the stop member so that the anchoring means rotates with the rotatable member;

said improvement further comprising forming the rotatable member united as part of the dental handpiece so that the rotatable member is in direct driving engagement with said driving means, and the dental handpiece further comprising a securing member movable to be locatable over the upper end of said bore to retain the anchoring means in the rotatable member against upward movement along the bore.

2. The combination according to claim 1 wherein the upper end of the rotatable member defines an annular seating for the turned over portion of the shank section, the stop member projecting upwardly from the seating.

3. The combination according to claim 1 wherein the longitudinal bore in the rotatable member is cylindrical and has a diameter substantially that of said shank section except over its upper end which tapers outwardly.

4. The combination according to claim 1 wherein the rotatable member carries gear teeth about its external periphery for driving engagement with said driving means.

5. The combination according to claim 1 wherein the rotatable member is formed with a downwardly extended portion at its lower end for supporting the shank section adjacent the pin section.

6. The combination according to claim 1 wherein the turned over portion is substantially L-shaped and of circular cross-section.

7. The combination according to claim 1 wherein the handpiece is self-contained and comprises a power source and the driving means whereby drive is transmitted from the power source to the rotatable member.

* * * * *